United States Patent [19]

Janda

[11] Patent Number: 5,384,252
[45] Date of Patent: Jan. 24, 1995

[54] MOLECULES WITH ANTIBODY COMBINING SITES THAT CATALYZE CARBOCYCLIC RING FORMATION FROM 5,6-ETHYLENICALLY UNSATURATED SULFONATE MOLECULES

[75] Inventor: Kim Janda, San Diego, Calif.

[73] Assignee: The Scripps Research Institute, La Jolla, Calif.

[21] Appl. No.: 179,253

[22] Filed: Jan. 10, 1994

[51] Int. Cl.$^6$ .......................... C12P 5/00; C12N 9/00; C12N 5/12

[52] U.S. Cl. ................. 435/166; 435/188.5; 435/240.27

[58] Field of Search .................. 435/188.5, 232, 233, 435/166, 240.27

[56] References Cited

U.S. PATENT DOCUMENTS 4,900,674  2/1990  Benkovic et al. .................. 435/232

OTHER PUBLICATIONS

Janda, K. D., et al. (1993) Science 259, 490–493.
Ashley, J. A., et al. (1992) J. Org. Chem 57, 6691–6693.
Li et al., *Science*, 264:1289–1293 (May 27, 1994).
Borman, *C&EN*, 3:43–44 (Jun. 13, 1994).

*Primary Examiner*—Charles L. Patterson, Jr.
*Attorney, Agent, or Firm*—Welsh & Katz, Ltd.

[57] ABSTRACT

The present invention contemplates monoclonal antibody combining site-containing molecules that catalyze the formation of a 6-membered ring compound from a 5,6-ethylenically-unsaturated-1-sulfonate substrate. The catalytic molecules bind to the substrate molecule as well as to a structural analog of the substrate that is a piperidine N-oxide whose nitrogen atom is in the same relative position in that ring as the sulfonate-bearing carbon atom of the open-chain substrate. A hybridoma that secretes the catalytic molecules and a process for forming a 6-membered ring compound that utilizes the catalytic molecules are also disclosed.

11 Claims, No Drawings

MOLECULES WITH ANTIBODY COMBINING SITES THAT CATALYZE CARBOCYCLIC RING FORMATION FROM 5,6-ETHYLENICALLY UNSATURATED SULFONATE MOLECULES

This invention was made with government support under Contract Nos. GM 43858 by the National Institutes of Health and CHE-9116377 by The National Science Foundation. The government has certain rights in the invention.

TECHNICAL FIELD

The present invention relates to antibodies, antigens and immunogens, and more particularly to paratope-containing molecules that catalyze carbocyclic ring formation from a 5,6-ethylenically unsaturated sulfonate molecule.

BACKGROUND OF THE INVENTION

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trysin (EC 3.4.21.4) or between (S)-2,3-epoxysqualene and lanosterol synthase (EC 5.4.99.7) in the formation of lanosterol. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding can lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively.

Slobin, *Biochemistry*, 5:2836–2844 (1966) reported preparing antibodies to a p-nitrocarbobenzoxy conjugate of bovine serum albumin. Those antibodies were thereafter used to hydrolyze p-nitrophenyl acetate and epsilon-aminocaproate esters. The reaction of the acetate ester was described by a second-order rate constant and was said to appear to be nonspecific. The second-order rate constant obtained using normal gamma globulin was said to be about equal to that of the specially prepared antibodies. The presence of the specially prepared antibodies was said to inhibit the hydrolysis of the aminocaproate ester.

Kohnen and coworkers also reported attempts using antibodies to catalyze esterolysis. The antibodies utilized by this group were, in each instance, raised to a portion of the ultimately utilized substrate molecule that did not contain the bond to be hydrolyzed.

In their initial work [*FEBS Letters*, 100:137–140 (1979) and *Biochim. Biophys. Acta*, 629:328–337 (1980)] anti-steroid antibodies were used to hydrolyze 7-umbelliferone (7-hydroxycoumerin) esters of a carboxyethyl thioether of asteroid. In each instance, an increase in hydrolytic rate was observed as compared to background or to a rate obtained with normal IgG. In both instances, turn over numbers were low (about one mole of substrates per mole of antibody per minute, or less), and the reaction rates declined with time, reaching a plateau with saturation of the antibody. That slow down in rate was attributed to an irreversible binding of the steroidal acid product to the antibody.

Kohen et al. also reported hydrolysis of 7-[-N-(2,4-dinitrophenyl)-6-aminohexanoyl]-coumerin using monoclonal antibodies raised to the dinitrophenyl portions of that substrate molecule [*FEBS Letters*, 111:427–431 (1980)]. Here, a rate increase over background was also reported, but the reaction was said to be stoichiometric rather than catalytic. A decrease in rate that approached zero was reported as saturation of the antibody was reached. Again, the decrease was attributed to product inhibition caused by binding of the product acid to the antibody since some of the initial hydrolysis activity could be regenerated by chromatography of an antibody-substrate-product mixture.

When strong antibody binding is directed to stable states of substrate molecules, the slow rate of dissociation of the complex impedes catalysis. Such is thought to be the situation for the results reported by Kohnen and coworkers.

The above constructs, though interesting, are severely limited by the failure to address the mechanism of binding energy utilization that is essential to enzymes [W. P. Jencks, *Adv. Enzymol.*, 43, 219 (1975)].

Those deficiencies can be redressed by using a transition state analog as the hapten to elicit the desired antibodies. This hapten (also referred to herein as an "analog ligand") can assume the role of an inhibitor in the catalytic system.

Thus, immunological binding can be used to divert binding interactions to catalytic processes. For example, it was suggested that use of an antibody to a haptenic group that resembles the transition state of a given reaction should cause an acceleration in substrate reaction by forcing substrates to resemble the transition state. Jencks, W. P., *Catalysis in Chemistry and Enzymology*, page 288 (McGraw-Hill, New York 1969). Notwithstanding that broad suggestion, specific transition state haptens were not suggested, nor were specific reactions suggested in which the concept might be tested.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolyric transition states cannot be isolated, a large amount of scientific literature has been devoted to the subject. Some of that literature is discussed hereinafter.

Whereas the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood. It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity, i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

Recently, Lerner, Tramontano and Janda [*Science*, 234, 1566 (1986)] reported monoclonal antibodies to hydrolyze esters in U.S. Pat. No. 4,659,567. Pollack, Jacobs and Schultz [*Science*, 234, 1570 (1986)] reported a myeloma protein denominated MOPC167 [Leon et al., *Biochem.*, 10, 1424 (1971)] that catalyzes the hydrolysis of a carbonate.

In the two Lerner and Tramontano disclosures, the antibodies were raised to a phosphonate that was synthesized to represent a stable analog of the tetrahedral hydrolyric transition state of the carboxylic acid ester or carbonate ester. The Pollack et al. antibody principally discussed was a myeloma protein that happened to bind to a phosphonate that was structurally analogous to the carbonate analog hydrolyzed. Thus, in the Lerner and Tramontano et al. work, the substrate to be hydrolyzed was preselected, with the immunizing analog and hydrolyric antibodies being synthesized in accordance with the desired product. Pollack et al. designed the substrate to be hydrolyzed once they knew the specificity of the myeloma protein. Pollack et al. also reported (above) the existence of a catalytic antibody, substrated and analog substrate system for carbonate hydrolysis similar in concept to that of Lerner et al. Work relating to that system is reported in Jacobs et al., *J. Am. Chem Soc.*, 109, 2174 (1987).

U.S. Pat. No. 4,888,281 (Schochetman et al.) discusses the possible use of antibodies as catalysts, and presents data relating to the use of polyclonal serum in hydrolyzing o-nitrophenyl-beta-D-galactoside. The antibodies useful in that patent are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turn over of the allegedly catalytic antibody was shown, nor was there an indication of the percentage of substrate galactoside cleaved. The patent did indicate that beta-D-galactosidase cleaved about ten times as much substrate as did the polyclonal antibodies, presuming linearity of absorbance at the unnamed concentration of substrate studied.

From the data presented in that patent, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

U.S. Pat. No. 4,792,446 (Kim et al.) discusses the possible use of antibody catalysts in the synthesis of chiral molecules. However, such syntheses were neither described nor disclosed in that patent.

In more recent work, bimolecular amide formation catalyzed by antibody molecules has been disclosed [Benkovic et al., *Proc. Natl. Acad. Sci. USA*, 85:5355 (1988)], as has an antibody-catalyzed Claisen rearrangement [Jackson et al., *J. Am. Chem. Soc.*, 110:4841 (1988)]. None of that work, nor the previously discussed work, has contemplated the use of antibodies to catalyze any reaction in a stereospecific manner.

Stereospecificity was shown in an antibody-catalyzed lactone-forming reaction [Napper et al., *Science*, 237:1041 (1987)] and in an antibody-catalyzed Claisen reaction [Hilvert et al., *Proc. Natl. Acad. Sci. USA*, 85:4955 (1988)].

U.S. Pat. No. 5,202,152 describes use of catalytic antibodies to catalyze a Diels-Alder (4+2) cycloaddition reaction. That catalyst binds to two substrate molecules, a conjugated diene and dienophile that react to form an intermediate that itself decomposes to expel a leaving group and form a 5- or 6-membered ring compound.

Antibody molecules were also reported as useful in catalyzing a disfavored cyclization of an epoxyalcohol to form a hydroxytetrahydropyran in Janda et al., *Science*, 259:490–493 (1993). In the latter disclosure, the catalytic antibodies were raised to a 6-membered cyclic N-oxide hapten to presumptively induce complementary charges in the antibody binding pocket while using the binding energy from substrate binding to organize the reaction geometry to favor the desired, disfavored 6-membered ring product over the usually obtained 5-membered ring product in that acid-catalyzed reaction. That acid-catalyzed reaction utilized a regioselective 6-endo-tet ring opening of an epoxide by an internal nucleophilic oxygen atom to form the ring.

BRIEF SUMMARY OF THE INVENTION

The present invention contemplates a receptor molecule that is a monoclonal antibody molecule or a molecule that contains an antibody combining site or paratope that catalyzes the formation of a 6-membered carbocyclic ring from an ethylenically unsaturated molecule by forming a carbon-to-carbon bond. The paratope of that molecule binds:

(a) to a substrate molecule having a hydrocarbon chain that contains ethylenic unsaturation and a carbon atom bonded to a sulfonate leaving group that are positioned within said chain such that said ethylenic unsaturation is at a 5,6-position in the chain relative to the sulfonate-bearing carbon atom; and (b) to an analog of said substrate molecule that is a piperidine N-oxide whose nitrogen atom is located at a ring position that is the same as that of the carbon atom bonded to the sulfonate in said substrate molecule, said N-oxide nitrogen atom being additionally bonded to a moiety that is structurally similar to said sulfonate, said analog containing at least two 6-membered rings.

A preferred substrate molecule to which a contemplated monoclonal molecule binds corresponds in structure to Formula I, below.

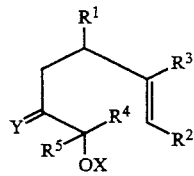

I wherein
OX is a sulfonate leaving group,
Y= is O= or (H—)$_2$,
R$^1$ is selected from the group consisting of hydrogen, C$_1$–C$_6$ alkyl and a terminating group T,
R$^2$ is hydrogen, a C$_1$–C$_{15}$ hydrocarbyl group, or a C$_5$–C$_{11}$ hydrocarbyl group containing a tri-C$_1$–C$_4$ alkylsilyl terminating group T,
R$^3$ is hydrogen or a C$_1$–C$_4$ alkyl group,
R$^4$ is hydrogen or a C$_1$–C$_4$ alkyl group, and
R$^5$ is hydrogen or a C$_1$–C$_4$ alkyl group, the sum of the carbon and silicon atoms in said R$^1$+R$^2$+R$^3$+R$^4$+R$^5$ is zero to 15; and (b) a preferred analog ligand having a structure corresponding to Formula II, below,

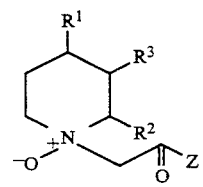

II wherein R$^1$, R$^2$ and R$^3$ are the same as R$^1$, R$^2$ and R$^3$ in a substrate of Formula I, and Z is a linking group that joins the haptenic analog ligand to an immunogenic carrier. The Z group is structurally similar to OX. The analog ligand also contains at least two 6-membered rings, or one ring and an R$^2$ hydrocarbyl group that can fold to mimic the structure of a 6-membered ring.

Exemplary OX sulfonate leaving groups include methanesulfonate, trifluoromethanesulfonate, benzenesulfonate, toluenesulfonate, nitrophenylsulfonate, methoxybenzenesulfonate and N-acetylamidophenylsulfonate moieties. An N-acetylamidophenylsulfonate moiety is particularly preferred. It is also preferred that R$^2$, R$^3$, R$^4$ and R$^5$ each be hydrogen and that Y= be two hydrogens [(H—)$_2$]. It is similarly preferred that R$^1$ be a dimethylphenylsilyl group.

Hybridoma molecules that secrete an above-defined monoclonal antibody are also contemplated. Hybridoma 4C6 that secretes a similarly designated monoclonal antibody is particularly preferred.

A process for catalytically forming a carbocyclic ring-containing product from an ethylenically unsaturated substrate is also contemplated, such a process comprises the steps of:

(a) admixing a catalytically effective amount of the monoclonal antibody molecules or paratope-containing portions thereof of as discussed above with above-discussed substrate molecules to which the monoclonal antibody molecules or paratope-containing portions thereof bind in a biphasic water-containing organic solvent in which the substrate molecules and the paratope-containing molecules are separately soluble to form a reaction mixture; and (b) maintaining the reaction mixture under biological reaction conditions for a time period sufficient for the 6-membered ring-containing product to form.

A process of preparing the above-described monoclonal receptor molecules is also contemplated. Here, a before-described haptenic analog ligand molecule is provided linked to an immunogenic carrier as a conjugate. The conjugate thus provided is dissolved or dispersed in a physiologically tolerably diluent to form an inoculum. The inoculum is introduced as by injection into a suitable, non-human mammalian host such as a mouse in an amount sufficient to induce antibodies to the haptenic analog ligand.

The antibodies so induced can be harvested. The harvested antibodies are assayed for their ability to bind to (immunoreact with) the immunizing, haptenic ligand analog. Regardless of whether or not the above harvesting step is carried out, immunoglobulin-producing cells such as those from the spleen of an immunized animal, such as an animal whose antibodies bind to the immunizing, haptenic analog ligand, are collected and are fused with myeloma cells to form hybridoma cells. The hybridoma cells are grown in a culture medium and the supernatant medium from the growing hybridoma cells is assayed for the presence of antibodies that bind to the immunizing, haptenic analog ligand.

Hybridoma cells whose supernatant contains such binding antibodies are then screened to determine which of those cells secrete antibodies that also catalyze a substrate into forming a 6-membered carbocyclic ring. Hybridoma cells whose secrete the desired catalytic antibodies that bind to the immunogen, bind to a substrate enol ester reactant ligand and catalyze carbocyclic ring formation are then cloned to provide the desired monoclonal antibodies from culture medium supernatant or from the ascites of a host mammal into which the hybridoma is introduced.

The present invention provides several benefits and advantages. One benefit of the invention is that desired cyclic molecules can be formed under relatively mild conditions in which such molecules do not otherwise form.

Another benefit of the present invention is that a desired compound can be formed in high yield.

An advantage of the invention is that a formed cyclic compound can be prepared as only a cis or trans isomer.

Yet another advantage of the present invention is that a desired catalyst can be readily prepared.

Still further benefits and advantages of the present invention will be apparent to those skilled in the art from the discussion that follows.

DETAILED DESCRIPTION OF THE INVENTION

I. Introduction

The present invention relates to molecules collectively referred to as receptors that are antibodies or paratope-containing (antibody combining site) portions induced by an analog of an ethylenically unsaturated sulfonate substrate. The analog ligand mimics the stereochemistry and conformation of the unisolatable transition state in the reaction pathway for the solvolytically-induced cyclization of that substrate. The receptor molecules (antibodies and antibody combining sites; i.e., paratope-containing molecules) that bind to the analog ligand and to the ethylenically unsaturated sulfonate substrate are thought to stabilize the cyclization transition state on the reaction pathway between a substrate reactant ligand and carbocyclic product, configurationally orient the bound substrate into a desired configuration for 6-membered ring formation, and exhibit catalytic properties in producing a desired 6-membered ring-containing product that is released from the catalyst after formation.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze reactions such as the hydrolysis of proteins by combining with the protein to stabilize the transition state of the hydrolysis or other reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W. P., *Adv. Enzymology*, 43, 219 (1975) and Pauling, L., *Amer. Scientist*, 36, 58 (1948)]. Support for this theory comes from the observation that substances that are thought to model the presumed transition states are often strongly bound to the enzymes as competitive inhibitors. Leinhard, G., *Science*, 180, 149 (1973) and Wolfenden, R., *Acc. Chem. Res.*, 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., *XVII International Solvay Conference* (November 1983)].

The converse proposition is that an antibody that is prepared to optimally bind a suitable analog of a transition state would function as a catalyst. The demonstration of this result by Lerner and co-workers and Schultz and co-workers in the previously cited papers completes the correlation of enzyme function and antibody structure and provides a useful approach to devising artificial enzymes.

The basic idea behind immunological catalysis described herein contemplates the use of analog ligands in the preparation of antibodies of predetermined specificity that preferentially bind to and thereby stabilize the transition state for cyclization upon binding to the specified substrate reactant ligand. An analog ligand simulates the conformation and some of the ionically charged species of a high energy transition state in a solvolytically-induced cyclization to induce the production of antibodies having the ability to bind related substrates and stabilize their 6-membered ring-forming reactions.

Such preferential binding and stabilization results in a reduction in the activation energy for the cyclization reaction, thus meeting a criterion for catalysis. Antibodies that display this property can be obtained by immunization with synthetic analogs that are chemically modified to resemble the charge and bonding characteristics of a substrate reactant ligand undergoing bond cyclization; i.e., by immunization with transition state analogs of the particular reaction.

In addition, a receptor molecule of the present invention also releases the formed product without itself reacting in a process referred to as turn over so that one antibody molecule can form several product molecules in a given time period. Such turn over meets another criterion for catalysis.

The mechanism by which an antibody catalyzes carbocyclic ring formation of a bound reactant ligand can be thought of in terms of an "induced fit" model. As the loosely bound substrate distorts or rearranges to conform to the binding geometry of the antibody, solvolysis of the sulfonate leaving group can begin, and stress and induced charge can be relieved by nucleophilic attack by and reorganization of the 5,6-ethylenic bond (anchimeric assistance) such that this reorganization leads to the opening of the double bond and donation of its electron pair to the forming carbonium on the carbon atom originally bonded to the sulfonate group.

The term "receptor" is used herein to mean a molecule that binds to a reactant ligand, inhibitor ligand, or analog ligand. The receptor molecules of the present invention are antibodies or other paratope-containing polyamide portions of an antibody.

Paratope-containing portions (antibody combining sites or idiotypes) of antibodies are those portions of antibody molecules that include the idiotype, and bind to the ligand or analog ligand. Such portions include the Fab, Fab', Fv and F(ab')$_2$ fragments prepared from antibodies by well-known enzymatic cleavage techniques. See for example, U.S. Pat. No. 4,342,566 to Theofilopoulos and Dixon, generally, and specifically, Pollack et al., [*Science*, 234, 1570 (1987)] who reported accelerated hydrolytic rates for Fab fragments were the same as those of the native immunoglobulin. Inasmuch as the antibodies from which paratope-containing positions are obtained are described as raised against or induced by immunogens, paratope-containing (antibody combining site-containing) receptors can also be discussed as being "raised" or "induced" with the understanding that a cleavage step is typically required to obtain an idiotype-containing polyamide from an antibody. Intact antibodies are preferred, however, and are utilized as illustrative of the receptor molecules of this invention.

The receptors useful in the present invention are monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monoclonal antibodies of the present invention are well known. Such receptors were first described by Kohler and Milsrein, *Nature*, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

A "ligand" is defined herein as a molecule that immunoreacts with or binds to a receptor molecule antibody combining site. Two types of ligand are contemplated herein. A first is termed an analog ligand and is used as an immunogen (hapten) when bonded to an appropriate immunogenic carrier to induce preparation of receptor molecules and as an inhibitor of the receptor molecule-catalyzed reaction when present without the carrier. The analog ligand is inert to undergoing the catalyzed reaction. The second ligand is referred to as the reactant ligand, substrate ligand, substrate or similar phrase and is a 5,6-ethylenically unsaturated sulfonate molecule that undergoes the catalyzed cyclization reaction. The substrate and analog ligands are structurally analogous.

As described herein, chemical analogs of substrate ligands are synthesized that incorporate a cyclic amine oxide at a specific, predetermined site relative to the rest of the molecule to mimic the conformation and developing carbonium ion charge of the transition state in the cyclization reaction. Further structural features of the analog ligand are discussed hereinafter.

Short polypeptide chains can induce the production of antibodies that recognize and bind to a homologous protein at a predetermined specific site. The present invention carries the earlier work with polypeptides a major step forward. Here, the antibodies (receptors) are induced by an immunizing haptenic first molecule (the analog ligand), and recognize and bind not only to that first molecule, but also to a second, structurally analogous molecule (the substrate reactant ligand).

In binding that second molecule, the receptor causes carbon-to-carbon bond formation in a cyclization reaction (which as demonstrated herein is catalytic) of preselected atoms to form a cyclic compound that corresponds in topology to the topology of the immunizing, haptenic first molecule. The correspondence in topology; i.e., size, shape, stereochemistry and charge, provides a means for preselecting the site at which bond formation in the reacting substrate ligand occurs. Inhibitor ligands that resemble the structure of an analog ligand or an reactant ligand are also bound by receptor molecules and do not undergo a reaction catalyzed by the receptor.

Consequently, by synthesis of a relatively small, immunizing haptenic analog ligand, one can induce the production of receptor molecules that recognize, bind to and catalytically form a ring in another molecule that can contain a plurality of 5,6-unsaturated sulfonates. Thus, a receptor can be prepared that causes cyclization between selected, predetermined carbon atoms of a model compound and yield a cyclic product.

The implication of this result is that one can confer the activity of hitherto known or unknown cyclase or synthase enzymes to immunoglobulins. Furthermore, the activity of the antibody combining site can be directed to any predetermined site at will by designating the bond to be formed by the cyclic amine oxide group placement in the haptenic analog ligand used for immunization.

Thus, antibodies and paratope-containing portions of antibodies are induced by a haptenic analog ligand cyclization transition state molecule.

II. Transition State of Esterolysis and Hapten (Analog Ligand) Design

Monoclonal antibody molecules or paratope-containing portions thereof that catalyze carbocyclic ring formation of an ethylenically unsaturated sulfonate molecule to form a 6-membered ring are contemplated here. The paratope binds:

(a) to a substrate molecule having a hydrocarbon chain that contains ethylenic unsaturation and a carbon atom bonded to a sulfonate leaving group that are positioned within the chain such that the ethylenic unsaturation is at a 5,6-position in the chain relative to the sulfonate-bearing carbon atom. The catalytic paratope also binds (b) to an analog of the substrate molecule that is a piperidine N-oxide whose nitrogen atom is located at a ring position that is the same as that of the carbon atom bonded to the sulfonate in said substrate molecule. The N-oxide nitrogen atom is additionally bonded to a moiety that is structurally similar to the sulfonate. The analog preferably contains at least two 6-membered rings.

Design of the analog ligand flows backward from the structure of the product to be formed through the transition state for bond formation to be mimicked, to the substrate and then to the analog ligand. The general reaction type of interest here will be discussed below, followed by a brief discussion of the products, and then more detailed discussions of the substrate and analog ligands to which a monoclonal catalytic molecule binds, as the structures of the substrate and analog ligands to which the catalyst binds define the catalyst.

The reactions catalyzed here are solvolytically-induced carbocyclic ring-forming reactions in which a carbon-to-carbon bond is formed. The natural model for these reactions is the formation of the tetracyclic lanosterol molecule from the open-chain 2,3-epoxysqualene molecule that is catalyzed by lanosterol synthase (EC 5.4.99.7).

A contemplated reaction has three distinct phases; i.e., initiation, propagation and termination. The initiation phase is begun by formation of a putative carbonium ion by ionization (solvolysis). The reaction is propagated by nucleophilic attack of the pi electrons of the ethylenic unsaturation that begin formation of the new carbon-to-carbon (C—C) bond and ring closure, with concomitant formation of another putative carbonium ion on the carbon of the double bond not involved in ring formation. The reaction terminates by elimination at the carbon adjacent the forming, putative carbonium ion and/or attack by an internal or external nucleophile at the carbon of the forming, putative carbonium ion. See, J. K. Sutherland in *Comprehensive Or-*

*ganic Synthesis*, B. M. Trost, ed., Vol. 3, Pergamon, (1991) pages 341–377.

Experimental evidence indicates that enzymatically-catalyzed lanosterol formation is initiated by opening of the squalene oxide epoxide ring with concomitant formation of a carbonium ion initiation center. That reaction is propagated by nucleophilic attack of the double bond at positions 5 and 6 from the carbonium ion formed on epoxide ring opening to form a C—C bond that becomes the lanosterol A ring. Attack on the initiation center leaves a relative positive charge (carbonium ion) on the 5-carbon, which is itself nucieophilically attacked by the next 5,6-positioned ethylenic unsaturation along the chain forming the B and C rings until the 5-membered D ring is formed by attack of the terminal 4,5-positioned double bond. The reaction terminated by nucleophilic attack of water. This enzymatically-catalyzed reaction is thought to proceed by a concerted reaction mechanism as mono-, bi- and tricyclic intermediates are not found, and the reaction proceeds in high yield and stereospecifically from a molecule with one chiral center to a molecule with seven chiral centers.

Enzyme-free studies of the solvolytic cyclization of mono-, di-, tri- and tetracyclic ring systems imply that mono- and some dicyclization reactions follow a concerted reaction mechanism. Enzyme-free studies of tri- and tetracyclic ring formation imply that although one or two constituent rings might form via a concerted mechanism, the completed molecules are formed stepwise. See, for example, P. A. Bartlett in *Asymmetric Syntheses*, J. D. Morrison, ed., Vol. 3, Chapter 5, Academic Press, Inc., New York (1984), pages 341–409.

The reaction contemplated here is the antibody paratope-catalyzed formation of a 6-membered carbocyclic ring. The contemplated products can be as simple as monocyclic compounds such as cyclohexene (Compound 16), cyclohexanol derivatives and α-ionone (Compound 25a) through di-, tri- and tetracyclic compounds such as progesterone (Compound 24a).

The cyclic product formed depends mostly upon the substrate molecule that must include a sulfonate group positioned 5- and 6-carbons away from the carbons of an ethylenic bond in a hydrocarbon chain. A further 6-membered ring that can be formed has ethylenic unsaturation 5- and 6-carbons away from the before-mentioned 5-carbon atom in a chain. Formation of a third ring can utilize a further ethylenic unsaturation at the 5,6-positions relative to the 5-carbon of the second-mentioned double bond, and so on. Where the natural trans-,anti,trans configuration of naturally occurring terpenoids and their derivatives such as progesterone is desired, the segments of the chain on either side of a double bond involved in ring formation are trans-bonded to those double bonds as is seen in squalene.

Although the present invention is concerned with the formation of 6-membered carbocyclic rings, 5- and 7-membered rings can also be formed catalytically as discussed herein. For formation of a 5-membered ring, the ethylenic unsaturation is located at the 4,5-positions relative to the 1-position sulfonate or other putative carbonium ion, whereas for 7-membered ring formation the ethylenic unsaturation is located at the 6,7-positions.

It is also to be understood that the analog ligand that induces the catalytic antibody and that catalyst itself play major roles in the reaction. However, unless the sulfonate and one or more double bonds are arrayed properly, a desired 6-membered ring cannot form.

More specifically, the substrate ligand molecule to which a monoclonal catalytic antibody paratope binds has a hydrocarbon chain that contains ethylenic unsaturation and a carbon atom bonded to a solvolyzable sulfonate leaving group. The sulfonate-bearing carbon atom can be anywhere in the chain but is arbitrarily assigned position 1 so that the position of the ethylenic unsaturation can be unambiguously assigned. The carbon atoms of that ethylenic unsaturation are located at chain positions 5 and 6 from the sulfonate-bearing carbon atom; i.e., the ethylenic unsaturation is at a 5,6-position relative to the 1-position sulfonate.

A substrate ligand can contain 6 to about 21 carbon atoms. Those atoms must include a chain of 6 carbons that include a 1-position sulfonate leaving group and 5,6-ethylenic unsaturation. Further ethylenic unsaturation and acetylenic unsaturation can be present. Where more than a single 6-membered ring is desired to be formed during the reaction, the position of any additional ethylenic double bond is as discussed previously; i.e., at a 5,6-position to the 5-carbon of a double bond that undergoes cyclization.

An open-chain substrate is preferred. However, one or more cyclic structures can be present and at least three carbon atoms of such a cyclic ring structure can be included in the hydrocarbon chain having a sulfonate at the 1-position and a 5,6-ethylenic double bond. Examples of such a substrate and its analog ligand are illustrated below as Compounds 20 and 20b, respectively, where OX and Z are as defined hereinafter.

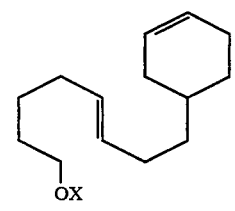

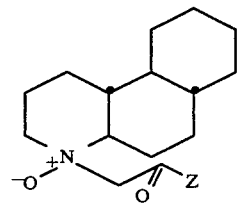

A preferred substrate to which the catalyst binds has a structure that corresponds to Formula I, below,

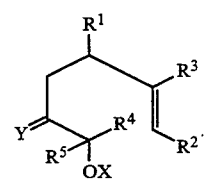

wherein
OX is a sulfonate leaving group,
Y= is O= or (H—)$_2$,
R$^1$ is selected from the group consisting of hydrogen, C$_1$–C$_6$ alkyl and a terminating group T$^1$, $R^2$ is hydrogen, a $C_1-C_{15}$ hydrocarbyl group, or a $C_5-C_{11}$ hydrocarbyl group containing a tri $C_1-C_4$ alkylsilyl terminating group $T^2$, $R^3$ is hydrogen or a $C_1-C_4$ alkyl group, $R^4$ is hydrogen or a $C_1-C_4$ alkyl group, and $R^5$ is hydrogen or a $C_1-C_4$ alkyl group, the sum of the carbon and silicon atoms in said $R^1+R^2+R^3+R^4+R^5$ is zero to 15.

In examining Formula I, it is seen that OX is a sulfonate leaving group. Sulfonate leaving groups are well known in the art and initial results indicate that it does not particularly matter which sulfonate leaving group is utilized. A relatively unreactive sulfonate leaving group was used illustratively herein to maximize differences between catalyzed and uncatalyzed reactions in that no reaction occurred in the uncatalyzed reaction. Exemplary useful sulfonate leaving groups include the methanesulfonate, trifluoromethanesulfonate, benzenesulfonate, toluenesulfonate, nitrophenylsulfonate, methoxyphenylsulfonate and N-acetylamidophenylsulfonate moieties. The N-acetylamidophenylsulfonate used illustratively here is preferred. The sulfonate leaving group, OX, can also be expressed as $-O_3SR^{10}$, where $R^{10}$ is the carbon-containing portion of the leaving group such as a methyl, trifluoromethyl, or nitrophenyl group, above.

The Y group of Formula I can be an oxygen atom so that Y= is O= so the substrate is a ketone. The Y group can also be two hydrogen atoms so that Y= can be depicted (H—)$_2$, making the 2-position carbon atom relative to the sulfonate-bearing carbon atom a saturated carbon atom. It is preferred that Y= be (H—)$_2$.

An $R^1$ group can be hydrogen, a $C_1-C_6$ alkyl or a terminating group $T^1$. Exemplary $C_1-C_6$ alkyl groups include methyl, ethyl, propyl, isopropyl, n-butyl, t-butyl, pentyl and hexyl.

A terminating or termination group $T^1$ is a group that fosters termination of the cyclization reaction. Hydrogen can be a terminating group where a proton is eliminated. However, several other well known terminating groups are preferred over hydrogen for use as an $R^1$ terminating group.

Exemplary, preferred, $T^1$ terminating groups are organosilyl groups. These terminating groups provide silyl cation leaving groups, which undergo elimination to provide ethylenic unsaturation to the cyclized product.

Such organosilyl groups include $C_1-C_4$ trialkylsilyl, $C_1-C_4$ alkyldiphenylsilyl, and di-$C_1-C_4$ alkylphenylsilyl groups. Methyl and ethyl are preferred $C_1-C_4$ alkyl groups. Exemplary organosilyl terminating groups include trimethylsilyl, triethysilyl, methyldiphenylsilyl and dimethylphenylsilyl groups.

Turning to $R^2$, it is seen that that group can be hydrogen, which is preferred and utilized illustratively here, a $C_1-C_{15}$ hydrocarbyl group or a $C_{11}$ hydrocarbyl group that contains a tri-$C_1-C_4$ alkylsilyl terminating group $T^2$.

A $C_1-C_{15}$ hydrocarbyl group, when present and containing at least four carbon atoms, is preferably ethylenically unsaturated where a second carbocyclic ring is to be formed fused to the first-formed ring, as in decalin or a derivative thereof. As noted before, that ethylenic unsaturation is located at a 5,6-position in the hydrocarbyl chain relative to the 5-position carbon atom depicted in Formula I. Additional ethylenic unsaturation can also be present along the chain in the same 5,6-relation to the 5-carbon of the second-noted ethylenic unsaturation as was noted before when additional rings are to be formed.

A preferred $R^2$ $C_1-C_{15}$ hydrocarbyl group is a $C_6-C_{15}$ hydrocarbyl group that includes acetylenic unsaturation as an internal or endogenous terminating group. A methylacetylenyl group (—$C_2$—$CH_3$) is particularly preferred as an internal terminating group when spaced two carbons from the nearest carbon of an ethylenic double bond. A methylacetyleneyl group can terminate a cyclization reaction by forming a 5-membered ring with a keto substituent as is present in progesterone. A similarly substituted 6-membered ring is formed when the methylacetylenyl group is positioned three carbons from the nearest carbon of a double bond.

An $R^2$ hydrocarbyl group can contain an open-chain that is straight or branched, and can include one or more ring structures. Compound 20 exemplifies an $R^2$ hydrocarbyl chain group that includes a ring structure. Exemplary branched chain substrates are illustrated in Table 1 hereinafter.

$R^2$ is preferably hydrogen. $R^3$, $R^4$ and $R^5$ are also preferably hydrogen.

The sum of the carbon and silicon atoms present in $R^1+R^2+R^3+R^4+R^5$ is zero to about 15, with about 9 atoms as are present in an $R^1$ dimethylphenylsilyl group being preferred. The basis for this size limitation and the previously noted carbon atom number limitations stem from the size of an antibody paratope or combining site.

An antibody combining site (paratope or binding pocket) is usually reported to be able to accommodate about 5–7 amino acid residues. A seven residue chain includes a chain of about 25 atoms including the N-terminal amino group (—$NH_2$) and C-terminal carboxyl group (—OH). Side chains must also be accommodated within the paratope.

That paratopic size is also about the size of a squalene oxide molecule (30 carbons) from which lanosterol is formed. In addition, Arevalo et al., Nature, 365:859–863 (1993) recently reported that the combining site of a non-catalytic monoclonal anti-progesterone antibody Fab' fragment designated DB3 could accommodate 81–91 percent of each of five steroidal molecules. That paper also noted that the steroidal D ring was embedded in a hydrophobic cavity at the bottom of the binding pocket of that paratope.

Extending the induced fit model for antibody binding to a steroid-forming reaction, the size of the substrate here is limited so that substantially all of the substrate; i.e., 80–100 percent, and particularly the ring-forming portion, can be within the catalytic paratope. Thus, the entire C-17 hydrocarbyl chain of lanosterol need not be bound. Such a size limitation can thereby utilize the binding energy of the antibody-substrate binding interaction to overcome otherwise contrary entropic effects present when forming three or four rings.

A substrate molecule preferably contains two 6-membered rings, one 6-membered ring plus a hydrocarbyl chain that can fold to approximate the shape and size (form) of a 6-membered ring, or a hydrocarbyl chain that can fold to approximate the form of two rings. The rings can be saturated or unsaturated, including aromatic unsaturation. The exemplary substrate used herein, Compound 15, below, (where Ph=phenyl, Me=methyl and Ac=acetyl) contains two aromatic rings and a hydrocarbyl chain (carbons 1-6) that can fold to approximate the form of a 6-membered ring.

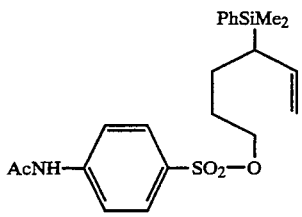

15

This two ring limitation stems again from the size of the catalytic antibody paratope. Thus, although smaller haptenic molecules that contain a single ring such as a molecule containing a nitrophenyl group can be used to induce and bind to antibodies, larger haptens that contain at least two rings, a ring and a chain or a chain of atoms sufficient to fold and approximate the form of at least two rings provide a better result.

Whether a hydrocarbyl group can be folded to approximate the form of one or more rings can be readily ascertained by a skilled worker. Two-dimensional line drawings as are seen in Table 1 hereinafter can be used to illustrate folding, as can molecular models and computer programs.

The presence of the at least two 6-membered rings or equivalent foldable structures in a substrate is discussed below in the discussion of the analog ligand as part of the structural analogy between the two molecules.

A hapten structurally analogous to a substrate is utilized to induce the production of catalytic antibodies. That hapten is referred to herein as an analog ligand or analog of the substrate, and in inducing production of a catalyst molecule, the catalytic paratope also immunoreacts with (binds to) the analog ligand.

As noted elsewhere, an analog ligand approximates an unisolatable transition state in the ring-forming reaction. Inasmuch as a concerted mechanism for initiating solvolysis/propagating ring formation/termination reaction is preferred because of the relative product homogeneity of the formed products, an analog ligand is constructed to be structurally analogous to a transition state structure on the reaction pathway that resembles the product. A 6-membered ring compound, whose atoms are in a configuration of a 6-membered ring to be formed, is therefore used as an analog ligand.

The initiating reaction here is solvolysis of the sulfonate leaving group. That solvolytic reaction forms a putative carbocation (carbonium ion) at the carbon atom to which the sulfonate leaving group was originally bonded. The analog ligand mimics that putative carbocation by use of an amine oxide whose positively charged nitrogen atom is at the position of the carbon atom of the substrate that was originally bonded to the sulfonate leaving group, having an adjacent, neutralizing negative charge.

Thus, putting the above two criteria together, where a 6-membered ring is to be formed, as here, the hapten is a piperidine N-oxide. Where a 5-membered ring is to be formed, the hapten is a pyrrolidine N-oxide, whereas for 7-membered ring formation, a hexamethyleneimine N-oxide is used as hapten.

To be an amine oxide, the nitrogen atom of a piperidine N-oxide must have yet another substituent group in addition to the two valences taken up by bonds to carbons in the ring and a bond to the oxygen atom. That fourth valence is occupied by a bond to a carbon atom of a substituent methylene carbonyl-Z group [—CH$_2$-C(O)—Z], where Z is a linking group for bonding the analog ligand to an immunogenic carrier.

It is preferred that the —CH$_2$C(O)—Z linking group be similar in structure to the sulfonate leaving group of the substrate ligand. Thus, although a sulfonyl (—SO$_2$—) moiety is larger than a carbonyl [—C(O)—] moiety, both contain a central atom and at least one oxygen. A methylene (—CH$_2$—) and an oxy (—O—) group are similar in size. A sulfonate leaving group, as is well known, must have a carbon-containing portion, R$^{10}$; several sulfonates being discussed earlier. The Z linking group thus contains a moiety, R$^{11}$ that is similar in structure to an R$^{10}$ group, so that the —CH$_2$C(O)—Z group is structurally similar to a sulfonate leaving group.

For example, where an alkyl group such as methyl or trifluoromethyl is R$^{10}$, the Z group contains an electrically neutral group of atoms such as a nitrogen of an amide and one or more methylenes, which form part of the linker. Exemplary of such linkers are —NH(CH$_2$)$_n$CO$_2$H groups, where n is an integer from 1 to about 9 to provide linkers such as glycine, β-alanine, 6-aminocaproic acid and 10-aminodecanoic acid. A —CH$_2$-C(O)—Z linking group can also be formed from the reaction of a 1-halo-2-keto-alkylene-ω-carboxylic acid such as chloro-acetoacetic acid or 5-bromo-4-acetyl-butyric acid.

Similarly, where the sulfonate R$^{10}$ group contains an aromatic ring such as the acetylamidophenyl ring of Compound 15 preferred here, the Z group also contains an aromatic ring. Exemplary —CH$_2$C(O)—Z groups are formed from suitably protected β-bromo-4-aminoacetophenone, α-chloro-4-carboxyacetophenone, p-(α-chloroacetyl)-phenylenediamine, p-(α-chloroacetyl)amidobenzoic acid and p-(α-chloroacetyl-)amidophenylacetic acid.

Each of the free termini of a linking group, Z, is preferably further reacted with spacer to provide distance between the carrier and hapten. A spacer can be an appropriate C$_2$–C$_6$ straight chain amino acid or a C$_4$–C$_6$ straight chain dicarboxylic acid such as β-alanine, 6-aminocaproic acid, glutaric acid or adipic acid for completion of the linking group so that that group is terminated with a carboxyl functionality for linkage to the immunogenic carrier.

A catalytic antibody need not and preferably does not bind to the complete sulfonate leaving group. As to the sulfonate portion, it appears as though only the carbon-linked oxygen atom and possibly one or a few atoms of the sulfonate need be bound by the catalytic paratope. As a consequence, structural congruity between R$^{10}$ and R$^{11}$ of the sulfonate leaving group and a Z group need not be exact, and a Z group is usually longer than the R$^{10}$ group of a sulfonate leaving group. A —CH$_2$-C(O)—Z group is thus said to be structurally similar to a sulfonate leaving group, —OX, rather than being structurally analogous.

The remaining substituents present on a substrate molecule are also present on an analog ligand, where possible. Thus, for example, the R$^1$, R$^2$ and R$^3$ groups of Formula I, above, are also present at the same relative position in an analog ligand; i.e., the nitrogen atom of the N-oxide function is considered to be position 1 of the analog ligand ring, so that the R$^1$, R$^2$ and R$^3$ groups present at positions 4, 6 and 5, respectively, in Formula I are present at positions, 4, 6 and 5 of an exemplary piperidine N-oxide ring.

R[4] and R[5] groups of a substrate of Formula I cannot be present in an analog of that substrate because there are not enough bonds available on a nitrogen atom to accommodate them. Similarly, where Y= is O= in Formula I, the corresponding Y= is (H—)$_2$ in the analog ligand as the corresponding structure, a quaternary hydroxamic acid, is not readily prepared.

The double bond of the substrate from which the new C—C bond is formed is also not present in the analog to the substrate. The absence of that ethylenic unsaturation again reverts to the analog ligand resembling a product-like transition state.

An analog ligand thus contains at least one fewer ethylenic unsaturations than does a substrate. Where a plurality of rings is to be formed from a substrate ligand, the analog to that substrate can contain one fewer carbon-to-carbon double bonds than the substrate for each ring to be formed. It is not necessary, however for each ring desired in the product to be present in the analog so long as the hydrocarbyl group R$^2$ of the analog can be folded to mimic the rings desired in the product.

The structure of an exemplary, preferred, analog ligand to which a catalytic paratope binds corresponds to that shown in Formula II, below,

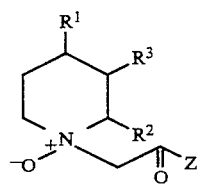

II wherein R$^1$, R$^2$, R$^3$ and Z are as before defined.

An analog ligand preferably contains at least two ring structures, or one 6-membered ring structure plus a hydrocarbyl substituent that can fold to approximate the structure of a 6-membered ring. One of those ring structures is the piperidine N-oxide ring where a contemplated 6-membered ring is to be formed, and that piperidine N-oxide ring is structurally analogous to the portion of the substrate molecule that contains the sulfonate leaving group. The second ring structure is either fused to the first ring, is present in a substituent terminating group, T$^1$, as in a dimethylphenylsilyl group, or the second ring is mimicked by an R$^2$ hydrocarbyl substituent that can fold to approximate the form of a 6-membered ring.

A preferred analog ligand is Compound 6 whose structure is illustrated below wherein Ph is phenyl and Me is methyl.

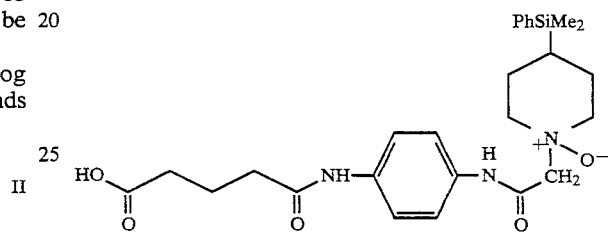

6

Exemplary substrate ligands, 6-membered ring-containing products and analog ligands are illustrated in Table 1, below, wherein a compound number is used for the substrate and that same number plus a letter is used for the corresponding product(s) and analog ligand(s), and OX and Z are as described before.

TABLE 1

| Substrate | Product | Analog Ligand |
|---|---|---|
| 20 | 20a | 20b |
| 21 | 21a | 21b |
| | | 21c |

TABLE 1-continued

| Substrate | Product | Analog Ligand |
|---|---|---|
| 22 | 22a | 22b |
| 23 | 23a, 23b | 23c |
| 24 | 24a | 24b |
| 25 | 25a | 25b |

Contemplated catalytic monoclonal antibody molecules or their paratope-containing portions bind to a before-defined substrate and analog ligand, and catalyze the solvolytic cyclization of the substrate to form a product containing a 6-membered ring. Contemplated monoclonal catalyst molecules preferably bind to a substrate that corresponds in structure to Formula I, above, and to an analog of the substrate having a structure that corresponds to Formula II, above.

Syntheses of a desired analog ligand and substrate can be carried out using well known organic chemical reactions such as those illustrated below and in the papers cited in J. K. Sutherland in *Comprehensive Organic Synthesis*, B. M. Trost, ed., Vol. 3, Pergamon, (1991) pages 341–377; P. A. Bartlett in *Asymmetric Synthesis*, J. D. Morrison ed., Academic Press, New York, Vol. 3 (1984) pages 341–409; and in Johnson, *Acc. Chem. Res.*, 1:1–8 (1968).

The synthesis of the exemplary hapten utilized herein when bound to an immunogenic carrier as an immunogen is illustrated hereinbelow in Scheme 1 for the preparation of Compound 6. Yields of the various reactions are shown after the compound number.

Standard abbreviations are utilized in Schemes 1 and 2 hereinafter are as follows: Bu=butyl, Ph=phenyl, Me=methyl, Boc=t-butoxycarbonyl, EtoH=ethanol, Bn=benzyl, MCPBA=m-chloroperbenzoic acid, TBSCl=tri-t-butylsilyl chloride, Et=ethyl, and Ac=acetyl.

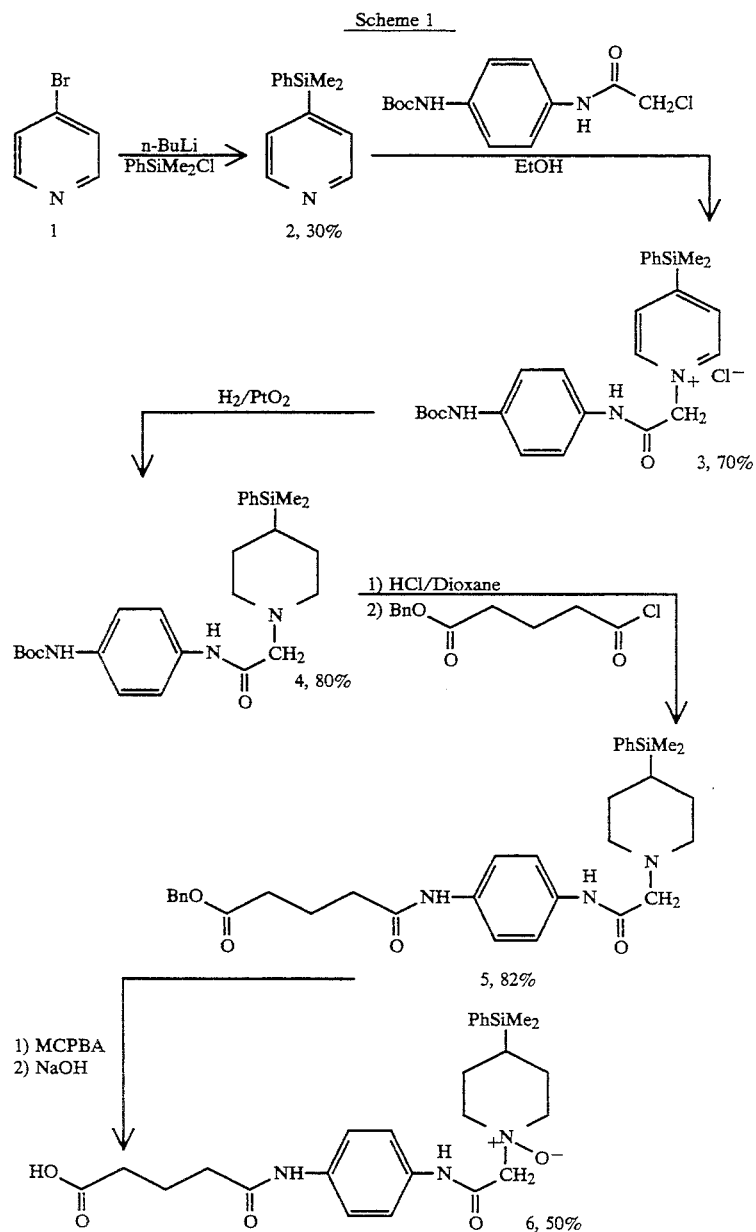

As is seen, 4-bromopyridine was reacted with n-butyl lithium and phenyldimethylsilyl chloride to produce Compound 2. Reaction of Compound 2 with 4-(N-t-Boc-amino)chloromethylanilide in ethanol provided the pyridinium salt, Compound 3. Reduction of that pyridinium salt with hydrogen using platinum oxide as catalyst provided the 4-substituted N-piperidine derivative shown as Compound 4. Reaction of Compound 4 in HCl/dioxane removed the N-t-Boc group, which was then replaced by reaction of benzyl glutaryl chloride to form Compound 5. Compound 5 was oxidized with m-chlorophenylperbenzoic acid (MCPBA) to form the amine oxide, which was followed by treatment with sodium hydroxide to cleave the benzyl group and form the acid salt that was then converted into the acid shown as Compound 6.

Compound 6 was reacted with keyhole limpet hemocyanin (KLH) as immunogenic carrier to form the immunogen used to induce catalytic antibodies, as is discussed hereinafter. Use of methyl 4-(chloroacetylamido)phenylacetate instead of 4-(N-t-Boc-amino)chloromethylanilide provides Compound 6a used as an inhibitor and in binding assays bound to BSA.

Scheme 2 illustrates the synthesis of illustrative substrate Compound 15. Individual yields for the reactions as illustrated in the scheme are provided with each numbered compound, as before.

Scheme 2

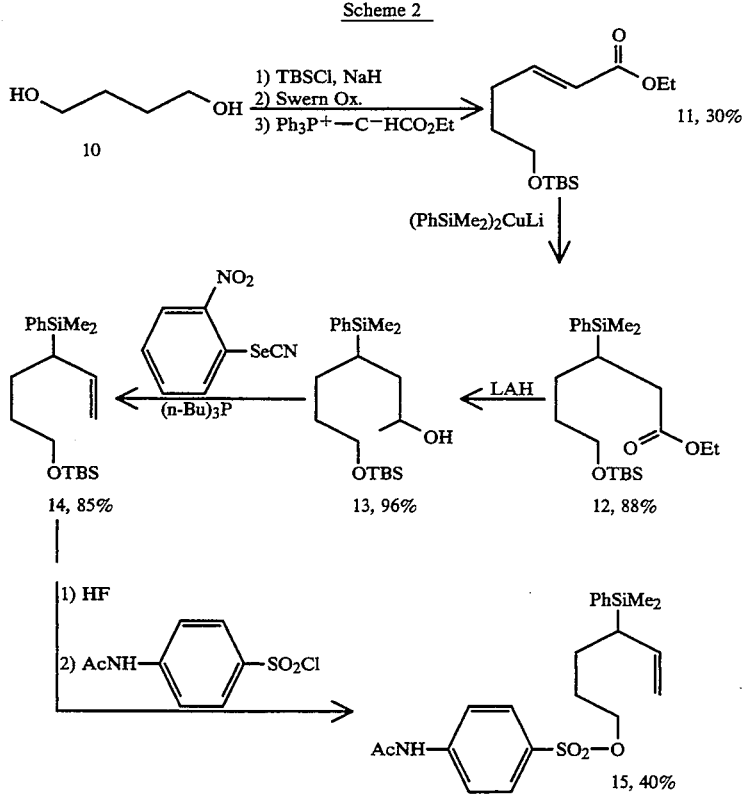

Thus, 1,4-dihydroxybutane, Compound 10, was first reacted with one equivalent of tri-t-butylsilyl chloride (TBSCl) in the presence of sodium hydride to block one of the hydroxyl groups. The resulting compound was subjected to Swern oxidation and was then reacted with the triphenylphosphene ylid in a Wittig reaction as shown to form Compound 11 in a total yield of 30 percent. Compound 11 was reacted with bisdimethylphenylsilyl cuprous lithium to form Compound 12. Reduction of Compound 12 with lithium aluminum hydride (LAH) provided hydroxyl Compound 13, which was reacted with o-nitrophenylselenylnitrile in the presence of tri-n-butylphosphene to form the unsaturated Compound 14. Reaction of Compound 14 with HF to remove the tri-t-butylsilyl group and then with acetamidophenylsulfonyl chloride formed Compound 15, the illustrative substrate utilized herein.

A contemplated monoclonal paratope (receptor) can be referred to as being biologically active. Biological activity of a receptor molecule is evidenced by the binding of the receptor to its antigenic reactant ligand, inhibitor ligand or analog ligand upon their admixture in an aqueous medium, at least at physiological pH values and ionic strengths. Preferably, the receptors also bind to an antigenic ligand within a pH value range of about 5 to 9, and at ionic strengths such as that of distilled water to that of about one molar sodium chloride.

In another embodiment, this invention relates to a process for forming a carbocyclic ring-containing product from an ethylenically unsaturated substrate. This process comprises the steps of:

(a) admixing a catalytically effective amount of the previously described catalytic monoclonal antibody molecules or paratope-containing portions thereof with substrate molecules to which those monoclonal antibody molecules or paratope-containing portions bind. The admixture is carried out in a biphasic water-containing organic solvent in which the substrate molecules and the paratope-containing molecules are separately soluble to form a reaction mixture.

The reaction mixture is maintained under biological reaction conditions for a time period sufficient for the 6-membered ring-containing product to form. The product is thereafter preferably isolated, but need not be isolated and can be utilized in the reaction medium for a further reaction or reactions.

A cyclization process of this invention utilizes a biphasic reaction medium as a portion of the reaction admixture. That medium typically contains water and buffer salts as one phase and an immiscible organic solvent such as pentane, hexane or heptane as the other, organic phase. The organic solvent must also not react with either the substrate, cyclic product or with the antibody molecules. Such interactions can be readily observed and are of little consequence to the skilled worker. In addition, the aqueous portion medium can contain other salts such as sodium chloride, as well as water-soluble calcium and magnesium salts as are frequently found in protein-containing media.

The substrate is soluble in the organic solvent phase of the medium, whereas, the catalytic antibodies or paratopic portions are soluble in the aqueous portion. The cyclic product is also soluble in the organic solvent phase. Although the proteinaceous catalyst and substrate/product are not grossly soluble in each other's solvent, some solubility, possibly at the interface of the two liquids, must occur as a contemplated reaction proceeds.

The aqueous and organic solvent phases are preferably present in volumes relative to each other of about 2:98 to about 20:80. More preferably, that volume:-volume ratio is about 5:95 to about 10:90 of aqueous phase to organic solvent phase.

The aqueous medium typically has a pH value of about 5 to about 9, and preferably about pH 6.0 to about 8.0. pH Values greater and less than those recited values can also be utilized so long as the catalyzed reaction is not substantially interfered with or inhibited.

The catalytic reactions are typically carried out at ambient room temperature; i.e., at about 20° to about 25° C. or at 37° C., and at an ambient atmospheric pressure; i.e., at about one atmosphere. However, temperatures down to about the freezing point of the aqueous medium and up to about the boiling point of the medium at atmospheric pressure can also be used. As is known, proteins such as the receptor molecule tend to denature at elevated temperatures such as those at which an aqueous medium boils, e.g., at about 100° C. and thus temperatures below about 40° C. are preferred. As is also well known, reactions that follow multimolecular kinetic expressions decrease in rate as the temperature decreases. Thus, a minimal temperature of about 15° C. is preferred.

The reactant ligand (substrate) is present in a reaction mixture in an amount up to its solubility in the organic solvent medium. Normally used concentrations of the reactant ligand are about 0.1 micromolar ($\mu$M) to about 10 millimolar (mM), with that amount also being a function of the solubility of the reactant ligand in the solvent medium. Where the product is desired, per se, relatively higher concentrations are used as compared to lower concentrations where a reaction mechanism or reaction kinetics are to be studies.

An effective amount of the catalytic receptor molecule is also present. That effective amount is typically a catalytic amount; i.e., the receptor is used at a molar ratio to the reactant ligand of about 1:2 to about 1:10,000, with a molar ratio of about 1:10 to about 1:100 being preferred. The ratio of receptor molecule to reactant ligand typically depends upon the specific activity of the receptor molecule toward the reactant ligand and the purpose of the user in running the reaction.

Thus, where the product is desired, a relatively higher concentration of receptor and higher receptor to reactant ligand ratio are used. Where the reaction mechanism or kinetics of the reaction are being studied, a lower concentration and ratio are typically used. A stoichiometric amount of receptor or more can also be used, but since the receptor is a catalytic molecule, use of even a stoichiometric amount can be wasteful. Thus, at least a catalytic amount of the receptor is utilized.

The admixture formed from mixing receptor molecules and reactant ligand molecules in a biphasic water-containing organic solvent reaction mixture is maintained for a time period sufficient for the binding and reaction to occur. The duration of that maintenance period is a function of several parameters including the receptor and reactant ligand selected, their concentrations, pH value, and temperature, as well as what is being sought from the reaction.

Thus, where kinetic studies are being carried out, maintenance times of minutes to hours are frequently encountered. Where the reaction products are desired, maintenance times of hours to days are more usual.

The biological reaction conditions are the temperature, pH value and presence of salts discussed before and in regard to a receptor molecule being biologically active.

III. Results

Analog ligand Compound 6 linked to KLH as an immunogen was used to immunize mice. Hybridomas were prepared using spleen cells from an immunized animal.

Twenty-six hybridomas were prepared whose secreted monoclonal antibodies (receptors) bound to Compound 6a (hereinafter). Of those twenty-six, four monoclonal molecules were found capable of catalytically reacting with substrate Compound 15 and were of the IgG isotype. The results of those reactions are illustrated in Table 2, below, for the reactions shown as catalyzed by each of monoclonal antibodies (MAb) 4C6, 16B5, 1C9 and 6H5 in the reaction of substrate Compound 15 in the formation of product Compounds 16 (formed by elimination of a termination group $T^1$) and 17 (formed by nucleophilic attack for termination), and the sulfonate leaving group, Compound 18.

TABLE 2

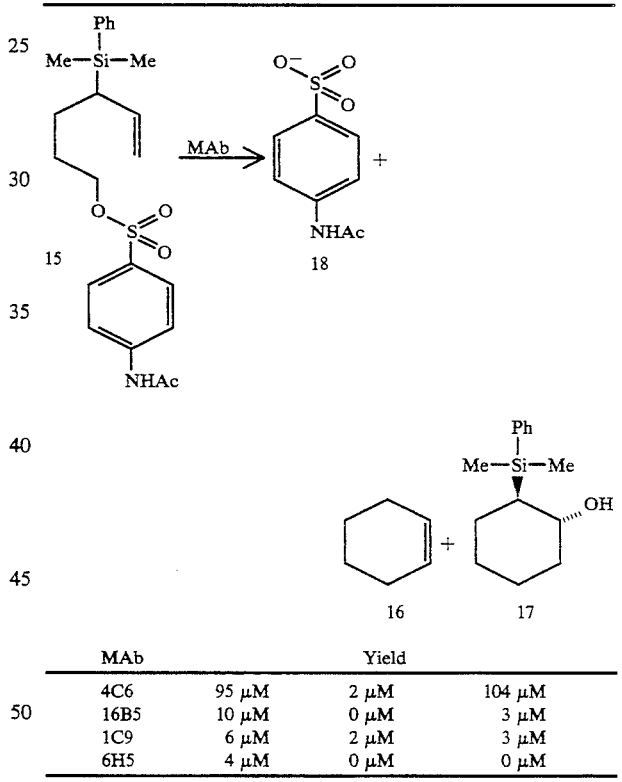

| MAb | | Yield | |
|---|---|---|---|
| 4C6 | 95 $\mu$M | 2 $\mu$M | 104 $\mu$M |
| 16B5 | 10 $\mu$M | 0 $\mu$M | 3 $\mu$M |
| 1C9 | 6 $\mu$M | 2 $\mu$M | 3 $\mu$M |
| 6H5 | 4 $\mu$M | 0 $\mu$M | 0 $\mu$M |

Hybridoma 4C6 and its monoclonal receptor were studied further. It was found that using 10 $\mu$M antibody in BisTris buffer at a pH value of 6.0 or 7.0 in a solvent containing 95:5 (v/v) hexanes:aqueous buffer could provide 100 $\mu$M of product formation in about 18 hours (overnight) at room temperature. That represented a conversion of about 40 percent of substrate, and evidenced turnover of the catalyst.

A value for $k_{cat}/k_{uncat}$ could not be obtained because no reaction took place in the absence of catalyst antibody. Values for $K_m$ and $k_{cat}$ were determined to be 72 $\mu$M and 0.006 min$^{-1}$, respectively. It was also found that a 100 $\mu$M amount of Compound 6a, below, completely inhibited the reaction.

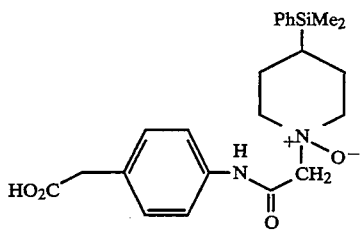

In comparative studies, formolysis of 1-hexen-6-ol sulfonate at 80° C. provided a 60 percent yield of 1-hexen-6-ol, 1 percent cyclohexene and 29 percent cyclohexanol. Additionally, attempted catalytic solvolysis of a saturated compound otherwise identical to Compound 15 provided no products.

The above results are interpreted to mean that monoclonal antibody 4C6 is a true catalyst for the desired carbocyclic ring formation. It is also inferred that this catalyzed reaction proceeds by a concerted reaction mechanism in view of the single, trans cyclohexanol derivative (Compound 17) that was formed.

This reaction is illustrated schematically below in Scheme 3, in which the transition state represented by bracketed Compound 15a is trapped by elimination of the silyl terminating group to form Compound 16 or nucleophilically attacked by water for termination to form the major product, Compound 17.

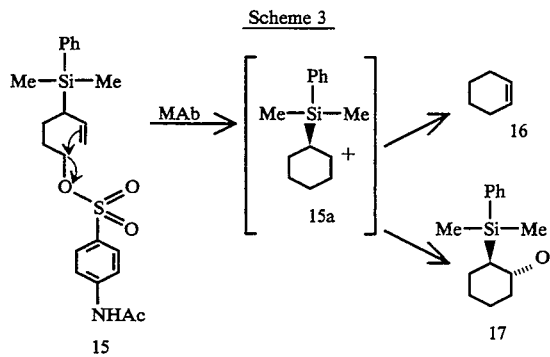

IV. Preparation of Conjugates and Inocula

Conjugates of haptenic analog ligand molecules with antigenic (immunogenic) protein carriers such as keyhole limpet hemocyanin (KLH) can be prepared, for example, by activation of the carrier with a coupling agent such as MBS (m-maleimidobenzoyl-N-hydroxysuccinimide ester), and coupling to the thiol group of the analog ligand. See, for example, Liu et at., Biochem., 80, 690 (1979). As is also well known in the art, it is often beneficial to bind a compound to its carrier by means of an intermediate, linking group.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the antigen than upon the determinant portion of the antigen, and is based upon criteria not particularly involved in the present invention. For example, if the conjugate is to be used in laboratory animals, a carrier that does not generate an untoward reaction in the particular animal should be selected.

The carrier-hapten conjugate is dissolved or dispersed in an aqueous composition of a physiologically tolerable diluent such as normal saline, PBS, or sterile water to form an inoculum. An adjuvant such as complete or incomplete Freund's adjuvant or alum can also be included in the inoculum. The inoculum is introduced as by injection into the animal used to raise the antibodies in an amount sufficient to induce antibodies, as is well known.

In an exemplary procedure, 2.5 mg of a reaction product of haptenic analog ligand Compound 6 or 6a in 250 μl of dimethylformamide is slowly added to 2 mg of KLH or BSA in 750 μl of 0.01M sodium phosphate buffer at a pH value of 7.2 in the presence of N-hydroxysuccinimidesulfonic acid and 1-ethyl-3-(dimethylaminopropyl)-carbodiimide coupling reagent. A temperature of 4° C. is utilized and the resulting admixture is stirred for about one hour to form the hapten-linked KLH or BSA conjugate.

V. Preparation of Monoclonal Receptors

The foregoing KLH conjugates (about 100 μg) were used to immunize mice (129G1X* strain), and monoclonal antibodies were obtained as described by Niman etal., Proc. Natl. Acad. Sci. USA, 77, 4524 (1980) and Niman et al., in Monoclonal Antibodies and T-Cell Products, Katz, D. H. ed., 23–51, CRC Press, Boca Raton, Fla. (1982). The lymphocytes employed to form the hybridomas of the present invention can be derived from any mammal, such as a primate, rodent (e.g., mouse or rat), rabbit, guinea pig, cow, dog, sheep, pig or the like. As appropriate, the host can be sensitized by injection of the immunogen, in this instance a haptenic analog ligand, followed by a booster injection, and then isolation of the spleen.

It is preferred that the myeloma cell line be from the same species as the lymphocytes. Therefore, fused hybrids such as mouse-mouse hybrids [Shulman et al., Nature, 276, 269 (1978)] or rat-rat hybrids [Galfre etal., Nature, 277, 131 (1979)] are typically utilized. However, some rat-mouse hybrids have also been successfully used in forming hybridomas [Goding, "Production of Monoclonal Antibodies by Cell Fusion," in Antibody as a Tool, Marchalonis et al., eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3X63Ag8U.1 (ATCC CRL 1597), Y3-Ag1.2.3. (deposited at Collection Nationale de Cultures de Microorganisms, Paris, France, number I-078) and P3X63Ag8 (ATCC TIB 9). The non-secreting murine myeloma line Sp2/O or Sp2/O-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were female 129G1X* mice bred in the mouse colony of The Scripps Research Institute, La Jolla, Calif.; however, when animals other than mice are used for preparation of the hybridomas, mice or that animal type can be used for the production of ascites fluid.

In particular, an exemplary monoclonal receptor was produced by the standard hybridoma technology of Kohler et al., Nature, 256, 495 (1975) and Engvall, E., Methods Enzymol., 70, 419 (1980). Specifically, female 129GIX* mice were immunized by intraperitoneal injection with an inoculum of 100 micrograms of conjugate (e.g., Compound 6 linked to KLH) mixed with RIBI adjuvant (MPL and TDM emulsion). Two weeks later, the mice were again injected in a like manner with 50 micrograms of the foregoing conjugate in PBS/alum. After an additional four-eight weeks, the mice were immunized intravenously with 50 micrograms of the conjugate. The spleens were removed from the mice, and the spleen cells were fused to myeloma cells.

The spleens cells were pooled and a single cell suspension was made. Nucleated spleen cells (about $1.4 \times 10^8$) were then fused with about $1.4 \times 10^2$ Sp2/0 and about $2.3 \times 10^8$ HL non-secreting myeloma cells in the presence of a cell fusion promoter (polyethylene glycol 2000). A hybridoma that produces a particular monoclonal antibody was selected by seeding the spleen cells in 96-well plates. Each well contains 150 $\mu$l Dulbecco's modified Eagle medium (DMEM) plus 2 percent bovine serum albumin (BSA, 1 percent nutridoma) hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against Compound 6a bound to BSA. Positive wells were cloned twice by limiting dilution. Those clones that continued to produce Compound 6a-specific antibody after two clonings were expanded to produce larger volumes of supernatant fluid. The hybridoma and the monoclonal receptors produced therefrom and described herein are identified by the laboratory designation as discussed herein.

The procedures used here for preparation of the conjugate, immunization and hybridoma formation and screening were substantially the same as those reported in Janda et al., Science, 259:490–493 (1993).

A monoclonal receptor of the present invention can also be produced by introducing, as by injection, the hybridoma into the peritoneal cavity of a mammal such as a mouse. Preferably, as already noted, syngeneic or semi-syngeneic mammals are used, as in U.S. Pat. No. 4,361,549, the disclosure of which is incorporated herein by reference. The introduction of the hybridoma causes formation of antibody-producing hybridomas after a suitable period of growth, e.g. 1-2 weeks, and results in a high concentration of the receptor being produced that can be recovered from the bloodstream and peritoneal exudate (ascites) of the host mouse.

Although the host mice also have normal receptors in their blood and ascites, the concentration of normal receptors is typically only about five percent that of the monoclonal receptor concentration.

Monoclonal receptors are precipitated from the ascitic fluids, purified by anion exchange chromatography, and dialyzed against three different buffers. The procedures used were as described in Janda et al., Science, 259:490–493, except that BisTris buffer was used.

Antibodies obtained are judged to be greater than 95 percent homogeneous by sodium dodecyl sulfate polyacrylamide gel electrophoresis [Laemmli, V. Nature, 227:680 (1970)]. The resulting concentrated solutions containing isolated IgG fractions were typically prepared into stock solutions of receptor at 1–20 mg/ml using an appropriate buffer such as 50 mM Tris-HCl, BisTris or sodium phosphate containing 0.01M sodium azide.

Of twenty-six anti-Compound 6a monoclonal receptors, one of the IgG isotype catalyzed the solvolytic cyclization Compound 15 to yield a product was studied further, as noted before. The hybridoma that produces the catalytic monoclonal receptor, given laboratory designation 4C6, was deposited at the American Type Culture Collection, 12301 Parklawn Drive, Rockville, Md. on Jan. 6, 1994 and was given ATCC accession number HB 11520.

The present deposit was made in compliance with the Budapest Treaty requirements that the duration of the deposit should be for 30 years from the date of deposit or for five years after the last request for the deposit at the depository or for the enforceable life of a U.S. patent that matures from this application, whichever is longer. The hybridoma will be replenished should it become non-viable at the depository.

A Fab fragment of a monoclonal receptor can De prepared from the purified receptor using predigested papain in a 0.1M sodium acetate buffer, at a pH value of 5.5, at 37° C., followed by reaction with iodoacetamide. The Fab fragment is typically further purified by anion exchange chromatography, dialysis, and DEAE anion exchange chromatography, and its homogeneity is judged by gel electrophoresis.

VI. Enzyme-linked Immunosorbent Assay (ELISA)

The binding of an analog ligand by the induced monoclonal receptor molecule was assayed by ELISA with antibody at a fixed concentration in the range of its titer and varying inhibitor (free Compound 6a) concentration. Use of free Compound 6a as inhibitor helps to assure that an observed binding interaction is antigen-specific.

Assays were performed in flat-bottom polyvinyl microtiter plates (Dynatech, Alexandria, Va.). Illustratively, the wells were coated with a solution comprising Compound 6a bonded to BSA (as Compound 6 it was bonded to KLH) as the antigen ligand in phosphate buffered saline (PBS) using 50 microliters of solution per well. BSA was used as a carrier to bind the hapten to the cell wall, and an analog ligand/BSA conjugate was used in place of the immunizing KLH-containing conjugate to screen out possible anti-KLH antibodies.

The bound ligands were coated at 1 microgram per milliliter. The plates were then incubated overnight at 37° C. in a dry oven. The dried plates were stored at 4° C. until use. Prior to the ELISA assay, dried plates were rehydrated by two washes of two minutes each with ten millimolar (mM) PBS, pH 7.4, containing 0.1 percent polyethylene sorbitan monolaureate (Tween 20) and 0.02 percent Thimerosal (sodium ethylmercurithiosalicylate), (Sigma, St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for one hour at 4° C. on a gyroshaker to contact the monoclonal antibody-containing supernatant with the bound Compound 6a. Following two washes of two minutes each, 50 microliters of peroxidase-labeled goat anti-mouse IgG+IgM (Tago, Burlingame, Ca.), diluted 1:1000, were added to each well, and the reaction mixture was incubated at 4° C. for one hour to bind the labeled antibody to bound monoclonal antibody.

The substrate used to assay bound peroxidase activity was prepared just prior to use and consisted of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution were added to each well, and color was allowed to develop for 15 minutes in the dark. Color development was stopped by adding 25 microliters of four molar $H_2SO_4$ to each well and the optical density at 492 nanometers (nm) was measured with a Multiskan ELISA plate reader.

For another preparation of the receptor molecules, the gene that encodes an antibody combining site-forming fragment can be obtained from any cell that produces an antibody molecule that immunoreacts as discussed herein. A preferred cell is a hybridoma cell.

For examples of general recombinant DNA cloning methods, see *Molecular Cloning*, Maniatis et al., Cold Spring Harbor Lab., N.Y., 1982; *DNA Cloning*, Glover, ed., IRL Press, McLean Va. (1985). For the genomic cloning and expression of immunoglobulin genes in lymphoid cells, see Neuberger et al., *Nature*, 312:604–8 (1984); Ochi et al., *Proc. Natl. Acad. Sci. USA*, 80:6351–55 (1987); and Oi et al., *Proc. Natl. Acad. Sci. USA*, 80:825–29 (1983). For cloning of immunoglobulin genes from hybridoma cells and expression in Xenopus oocytes, see Roberts et al., *Protein Engineering*, 1:59–65 (1986), and see Wood et al. for expression in yeast. *Nature*, 314:446-9 (1985).

Assays for formation of product Compounds 16 and 17 were carried out by gas chromatography, whereas the sulfonate product, Compound 18, was identified on a C-18 reversed phase HPLC column. Aliquots were taken directly from the organic or aqueous phases, respectively, and analyzed by direct injection to either machine.

Physical data for Compounds 6, 15 and 17 are provided below.

Compound No. 6:

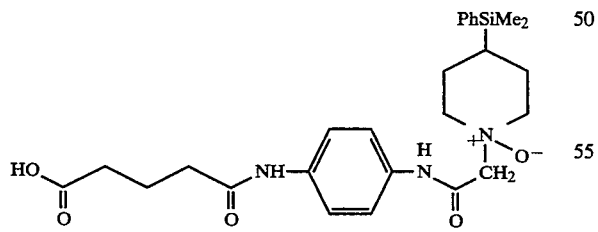

NMR ($CD_3OD$, 300 $MH_2$)δ0.35 (S, 6H) , 1.14 (tt, 1H, J=3.0, 13.3 Hz), 1.78–2.10 (m, 6H) 2.38 (t, 2H, 7.3 Hz), 2.42 (t, 2H, J=7.3 Hz), 3.77 (dt, 2H, J=2.7, 12.6 Hz). 3.98 (d, 2H, J=12.3 Hz), 4.47 (s, 2H), 7.35–7.40 (m, 3H), 7.50–7.58 (m, 6H).

Mass Spectrum: HRMS (FAB, NaI) Calculated for [$C_{26}H_{35}N_3O_5S_1$+Na] 520.2244 Found: 520.2267

Compound No. 15:

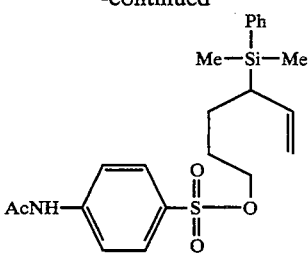

NMR ($CD_3ON$, 300 MHz):δ0.19 (s, 6H), 1.2–1.7 (m, 5H), 2.10 (s, 3H) 3.93 (t, 2H, J=5.6 Hz) , 4.72 (dd, 1H, 1.1, 17 Hz), 4.82 (dd, 1H, 2.0, 10.3 Hz), 5.48 (dt, 1H, 10.1, 17.9 Hz), 7.30–7.48 (m, 5H), 7.70–7.80 (m, 4H), 8.71 (s, 1H).

Mass Spectrum: HRMS (FAB) Calculated for ($C_{22}H_{29}NO_4SSi$+M)=432.1665 Found: 432.1675

Compound No. 17:

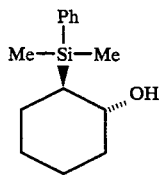

NMR Data: ($CDCl_3$, 300 MHz)δ0.34 (s, 3H), 0.35 (s, 3H), 0.86 (dt, 1H, J=3.3, 10.5 Hz), 1.0–1.3 (m, 4H), 1.6–2.0 (m, 4H), 3.42 (dt, 1H, J=4.0, 10.1 Hz) 7.39–7.40 (m, 3H), 7.55–7.60 (m, 2H).

Mass Spectrum: HRMS (FAB, NaI): Calculated for ($C_{14}H_{22}SiO$+Na)=257.1338 Found: 257.1330

The foregoing is intended as illustrative of the present invention but not limiting. Numerous variations and modifications can be effected without departing from the true spirit and scope of the invention.

What is claimed:

1. Monoclonal antibody molecules or paratope-containing portions thereof that catalyze carbocyclic ring formation of an ethylenically unsaturated sulfonate molecule to form a 6-membered ring, said paratope binding:
   (a) to a substrate molecule having a hydrocarbon chain that contains ethylenic unsaturation and a carbon atom bonded to a sulfonate leaving group that are positioned within said chain such that said ethylenic unsaturation is at a 5,6-position in the chain relative to the sulfonate-bearing carbon atom; and
   (b) to an analog of said substrate molecule that is a piperidine N-oxide whose nitrogen atom is located at a ring position that is the same as that of the carbon atom bonded to the sulfonate in said substrate molecule, said N-oxide nitrogen atom being additionally bonded to a moiety that is structurally similar to said sulfonate, said analog containing at least two 6-membered rings or one 6-membered ring structure plus a hydrocarbyl substituent that can fold to approximate the structure of a 6-membered ring.

2. The monoclonal molecules of claim 1 secreted by hybridoma 4C6 having ATCC accession number HB 11520.

3. Monoclonal antibodies or paratope-containing portions thereof that catalyze the cyclization of an ethylenically unsaturated molecule to form a carbon-to-carbon bond in a 6-membered ring, said paratope binding:
(a) to a substrate molecule having a structure corresponding to the formula

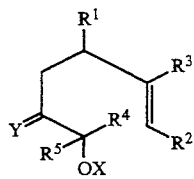

wherein
OX is a sulfonate leaving group,
Y= is O= or (H—)$_2$,
$R^1$ is selected from the group consisting of hydrogen, $C_1$-$C_6$ alkyl and a terminating group T,
$R^2$ is hydrogen, a $C_1$-$C_{15}$ hydrocarbyl group, or a $C_5$-$C_{11}$ hydrocarbyl group containing a tri $C_1$-$C_4$ alkylsilyl terminating group T,
$R^3$ is hydrogen or a $C_1$-$C_4$ alkyl group,
$R^4$ is hydrogen or a $C_1$-$C_4$ alkyl group, and
$R^5$ is hydrogen or a $C_1$-$C_4$ alkyl group, the sum of the carbon and silicon atoms in said $R^1+R^2+R^3+R^4+R^5$ is 4–15; and
(b) an analog ligand having a structure corresponding to the formula

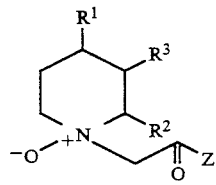

wherein $R^1$, $R^2$ and $R^3$ are the same as $R^1$, $R^2$ and $R^3$ above and Z is a linking group to an immunogenic carrier, the depicted —CH$_2$C(=O)—Z group being structurally similar to OX, said analog ligand having at least two 6-membered rings or one 6-membered ring structure plus a hydrocarbyl substituent that can fold to approximate the structure of a 6-membered ring.

4. The monoclonal molecules of claim 3 wherein $R^2$, $R^3$, $R^4$ and $R^5$ are each hydrogen.

5. The monoclonal molecules of claim 4 wherein $R^1$ is dimethylphenylsilyl.

6. The monoclonal molecules of claim 3 wherein OX is a sulfonate leaving group selected from the group consisting of methanesulfonate, trifluoromethanesulfonate, benzenesulfonate, toluenesulfonate, nitrophenylsulfonate, methoxyphenylsulfonate and N-acetylamidophenylsulfonate moieties.

7. The monoclonal molecules of claim 3 wherein OX is an N-acetylaminophenylsulfonate moiety.

8. The monoclonal molecules of claim 3 wherein $R^1$ is a terminating group selected from the group consisting of a tri-$C_1$-$C_4$ alkylsilyl or a di-$C_1$-$C_4$ alkylphenylsilyl group.

9. A hybridoma that secretes monoclonal antibody molecules containing a paratope that catalyzes the carbocyclic ring formation of an ethylenically unsaturated molecule to form a carbon-to-carbon bond in a 6-membered ring, said paratope binding:
(a) to a substrate molecule having a hydrocarbon chain that contains ethylenic unsaturation and a carbon atom bonded to a sulfonate leaving group that are positioned within said chain such that said ethylenic unsaturation is at a 5,6-position in the chain relative to the sulfonate-bearing carbon atom; and
(b) to an analog of said substrate molecule that is a piperidine N-oxide whose nitrogen atom is located at a ring position that is the same as that of the carbon atom bonded to the sulfonate in said substrate molecule, said N-oxide nitrogen atom being additionally bonded to a moiety that is structurally similar to said sulfonate, said analog containing at least two 6-membered rings or one 6-membered ring structure plus a hydrocarbyl substituent that can fold to approximate the structure of a 6-membered ring.

10. The hybridoma molecule of claim 9 designated 4C6 having ATCC accession number HB 11520.

11. A process for catalytically forming a carbocyclic ring-containing product from an ethylenically unsaturated substrate comprising the steps of:
(a) admixing a catalytically effective amount of the monoclonal antibody molecules or paratope-containing portions thereof of claim 1 with substrate molecules to which said monoclonal antibody molecules or paratope-containing portions thereof bind in a biphasic water-containing organic solvent in which said substrate molecules and the paratope-containing molecules are separately soluble to form a reaction mixture; and
(b) maintaining said reaction mixture under conditions suitable for said process to occur for a time period sufficient for said 6-membered ring-containing product to form.

* * * * *